United States Patent [19]

Brustad

[11] Patent Number: 5,335,647
[45] Date of Patent: Aug. 9, 1994

[54] POTTED ENDOSCOPE

[75] Inventor: John R. Brustad, Dana Point, Calif.

[73] Assignee: Applied Medical Resources Corporation, Laguna Hills, Calif.

[21] Appl. No.: 886,975

[22] Filed: Jun. 26, 1992

[51] Int. Cl.5 .................................. A61B 1/00
[52] U.S. Cl. ........................................ 128/4; 385/117
[58] Field of Search ............... 128/4, 6; 385/115, 116, 385/117, 103, 104

[56] References Cited

U.S. PATENT DOCUMENTS

| 4,076,377 | 2/1978 | Moraschetti | 385/116 |
|---|---|---|---|
| 4,279,245 | 7/1981 | Takagi et al. | 128/4 |
| 4,772,093 | 9/1988 | Abele et al. | 385/117 X |
| 4,784,464 | 11/1988 | Ouchi | 385/115 X |
| 4,790,295 | 12/1988 | Tashiro | 128/6 |
| 4,807,597 | 2/1989 | Tsuno et al. | 128/6 |
| 4,813,400 | 3/1989 | Washizuka | 128/6 |
| 4,867,529 | 9/1989 | Utsumi et al. | 385/117 |
| 5,073,048 | 12/1991 | Adachi et al. | 385/115 |

Primary Examiner—Richard J. Apley
Assistant Examiner—Karen A. Jalbert
Attorney, Agent, or Firm—Richard L. Myers

[57] ABSTRACT

An endoscope includes a handle assembly and an elongate probe defining a channel which extends to a distal end of the endoscope. A fiber is disposed in the channel and has a failure mode characterized by a first bending radius. The channel is potted with a compound which distributes bending stresses along the fiber providing the fiber with a failure mode characterized by a second bending radius shorter than the first bending radius. An associated method includes the step of potting the channel with an epoxy having, in a cured state, a durometer of about Shore 70A.

17 Claims, 2 Drawing Sheets

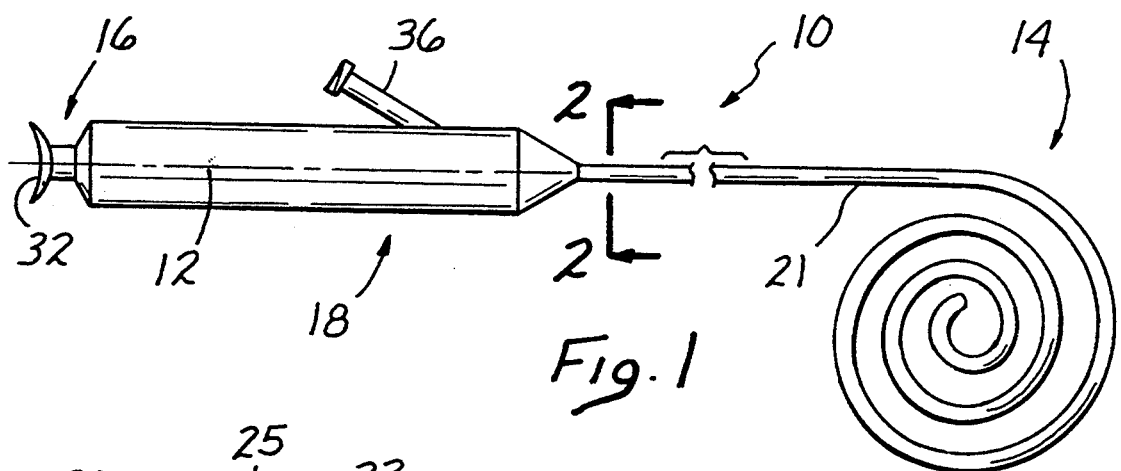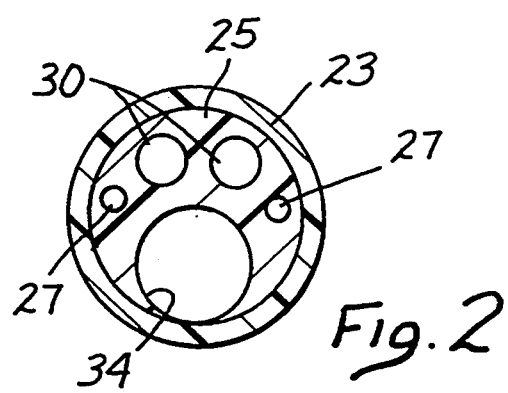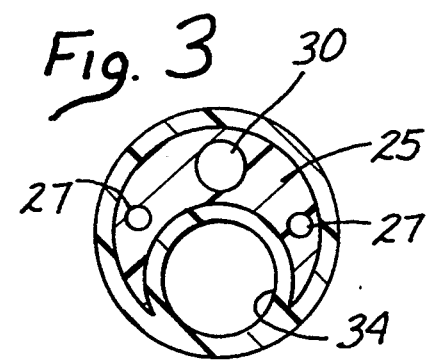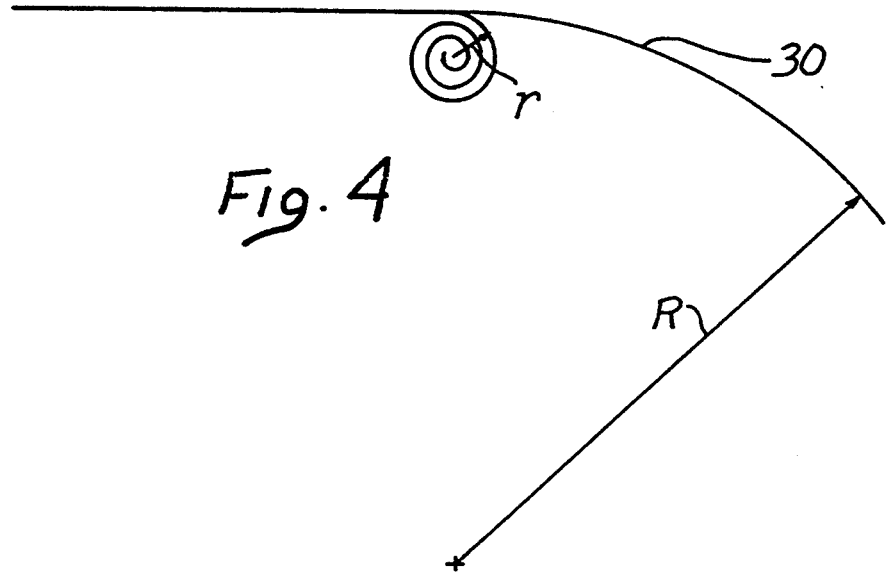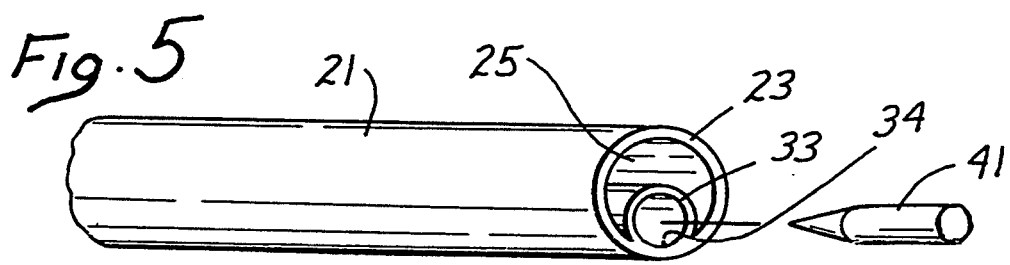

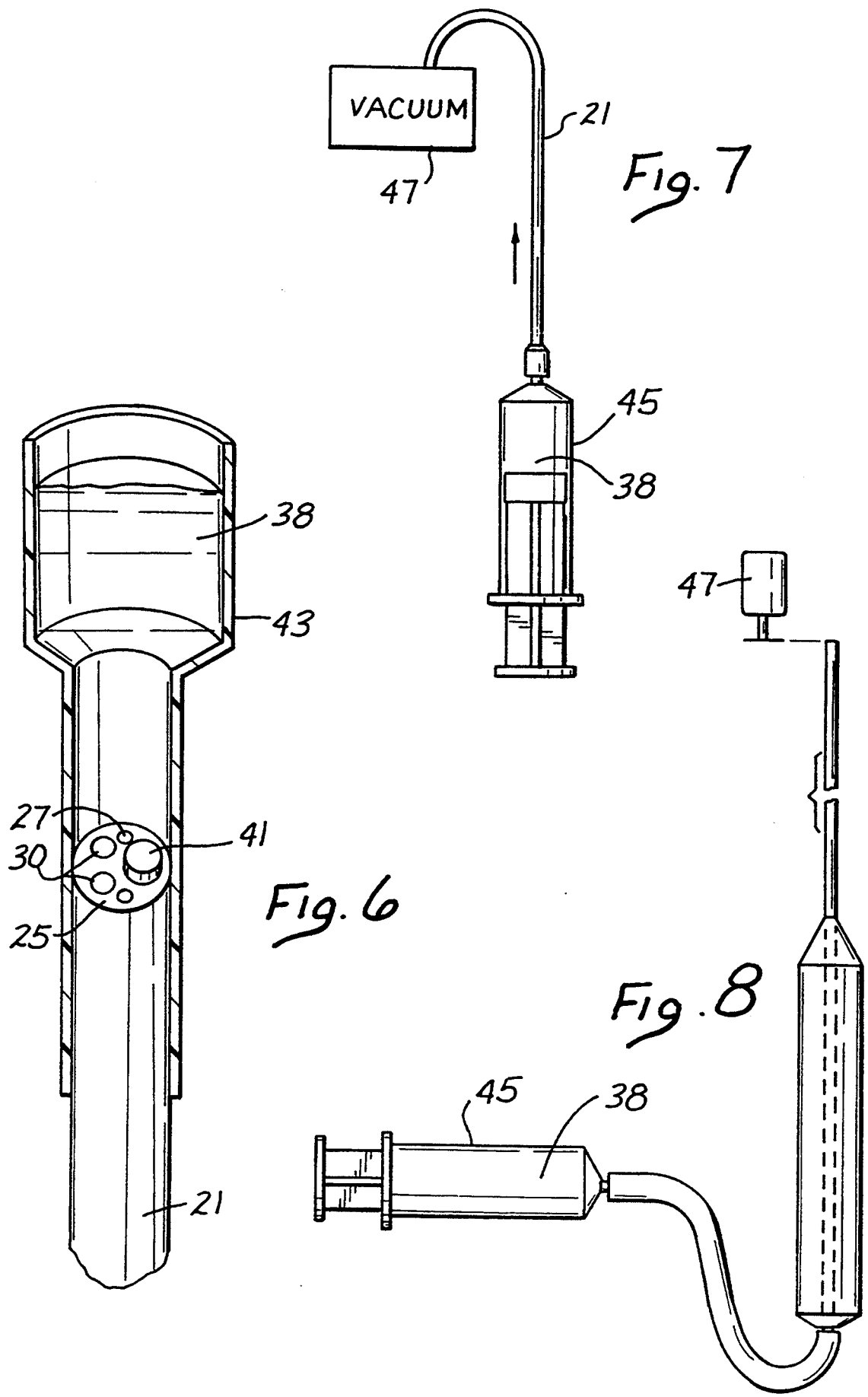

POTTED ENDOSCOPE

BACKGROUND OF THE INVENTION

1. Field of the Invention

This invention relates generally to endoscopes, sometimes referred to merely as scopes, and more specifically to endoscopes including fiberoptics, electrical wires, conduits and other elongate objects collectively referred to herein as fibers.

2. Discussion of the Prior Art

An endoscope is a surgical instrument having an elongate probe that carries optical fibers from a proximal end of the scope to a distal end of the scope. When the probe is inserted into the body, the optical fibers provide the user with a view of the regions interior of the body. Typically the optical fibers extend through a channel that is formed by a handle assembly and the probe of the endoscope. The scope may also include other channels, lumens or conduits to facilitate the manipulation of various instruments which are adapted for insertion through the endoscope.

Endoscopes are generally categorized in two forms, rigid and flexible. Flexible scopes tend to conform to the body anatomy, while rigid scopes tend to conform the body anatomy to the scope. With both of these types of scopes, bending of the probe commonly occurs. This is certainly the case with the flexible scopes but even the rigid scopes may experience some bending. When the probe of the scope bends, so does its channel and the enclosed fibers. Depending on the nature of a fiber, the stresses associated with bending may degrade its performance characteristics. This degradation may take the form of reduced optical properties or a failure mode resulting from the breaking of the fiber. This is particularly common with optical fibers which tend to break when bent along a radius shorter than three inches, for example. When a fiber breaks, the entire endoscope is rendered useless and requires that a significant expense be incurred to purchase a new endoscope.

SUMMARY OF THE INVENTION

In accordance with the present invention, a material is provided around the fibers of the scope to provide relief from bending stresses. This material may include a potting compound, such as an epoxy which has a long potting time and is curable to a relatively low durometer. If any portion of the channel is potted the fiber will be stress relieved at least in that portion. Improved bending characteristics, short of the failure mode, have been experienced with a bending radius reduced from three inches to one-half inch in a typical example.

In accordance with one aspect of the invention, an endoscope having a distal end and a proximal end includes a handle assembly, and an elongate probe extending distally of the assembly and having characteristics for being bent. Portions of the probe define a channel extending along the endoscope, which is configured to receive a fiber having an adverse response to bending stresses associated with a particular radius of bending of the probe. Means is disposed around the fiber in the channel for distributing the bending stresses along the fiber to avoid the adverse response at the particular radius of bending.

In another aspect of the invention a method for making an endoscope includes the step of providing a handle assembly and bendable probe defining a channel along the length of the endoscope. A fiber having adverse characteristics in response to stresses associated with a particular radius of bending, is inserted into the channel. Finally, the channel is injected with a potting compound having characteristics for distributing the bending stresses in the fiber to inhibit the adverse characteristics at the particular radius of bending.

These and other features and advantages of the invention will be more apparent with a discussion of preferred embodiments and the best mode of the invention, taken in combination with the associated drawings.

DESCRIPTION OF THE DRAWINGS

FIG. 1 is a side view of an endoscope including the handle assembly and probe defining a potted channel in accordance with one embodiment of the present invention;

FIG. 2 is a radial cross-section view of the probe taken along lines 2—2 of FIG. 1;

FIG. 3 is a radial cross-section view similar to FIG. 2 and illustrating an additional embodiment of the present invention;

FIG. 4 is a schematic view of the probe of an endoscope illustrating the reduced radius of curvature provided in accordance with the present invention;

FIG. 5 is a perspective view of an endoscopic probe having a working channel, and a plug inserted into the channel in accordance with one step in a process for making an endoscope;

FIG. 6 is a perspective view of a plugged endoscopic probe and a cross-section view of a funnel suitable for potting a channel of the probe;

FIG. 7 is a side view of a step for potting the probe by injecting a potting compound vertically into the channel; and FIG. 8 is a side view illustrating a step for potting a channel which extends through the probe and the handle assembly associated with an endoscope.

DESCRIPTION OF PREFERRED EMBODIMENTS AND BEST MODE OF THE INVENTION

An endoscope is illustrated in FIG. 1 and designated generally by the reference numeral 10. The endoscope is representative of any medical device having an elongate probe which carries fibers in a channel and is subjected to bending of the probe. Included within this general category are specific types of endoscopes such as cystoscopes, resectoscopes, and ureteralscopes.

The endoscope of FIG. 1 has an elongate configuration and extends along an axis 12 between a distal end 14 and a proximal end 16 of the endoscope. A handle assembly 18 is disposed at the proximal end 16 and a probe 21 extends from the handle assembly 18 to the distal end 14.

In its simplest form, the probe 21 comprises a tube 23, best illustrated in FIG. 2. This tube 23 defines an interior channel 25 between the handle assembly 18 and the distal end 14. Optical fibers, including at least one light fiber 27 and one image fiber 30, are typically disposed in the channel 25. These fibers 27, 30 are representative of many types of elongate structures which can be disposed within the channel 25 of the endoscope 10. Other types of fibers might include electrical conductors or various conduits each of which has performance characteristics which tend to degrade if the probe 21 and channel 25 are bent. In the case of the optical fibers 27 and 30, the optical characteristics of the fibers can degrade with bending. If the bending is particularly severe, the fibers 27, 30 may reach a failure mode associated with the breaking of the fiber.

The fibers 27 and 30 extend through the probe 21 and the handle assembly 18 to an eyepiece 32 at the proximal end 16 of the endoscope 10. When the probe 21 is introduced into a body cavity, objects in proximity to the distal end 14 are illuminated by the light fibers 27 and the resulting images are transmitted to the eyepiece 32 through the image fiber 30. In the illustrated embodiment, the probe 21 also includes an inner wall 33 which defines a working channel or lumen 34 which can be accessed through a side port 36 in the housing 18. Various instruments such as cutters and graspers can be inserted through this working channel 34 to perform various operations at the distal end 14.

Optical fibers are particularly susceptible to breaking as they are commonly formed from glass which is known to be very brittle. The bending of an optical fiber, such as the light fiber 27 or image fiber 30 can easily result in breaking which renders the fiber totally dysfunctional. By way of example, it is noted that an optical fiber formed of quartz and having a diameter of one-half millimeter is highly susceptible to breaking with a bending radius of only about three inches. If the probe 21 of the endoscope 10 were subjected to this degree of bending, it would very likely result in breaking of the fibers 27, 30 and render useless the entire endoscope 10.

In accordance with the present invention, a potting compound is disposed within the channel 25 of the probe 21. This potting compound will closely engage the fibers 27, 30 and provide for an axial distribution of bending stresses- In effect, the potting compound 38 distributes these stresses along the fibers 27, 30 with the result that the probe 21 can be bent along a significantly shorter radius without degrading the performance of the fibers 27, 30. Continuing with the example of a quartz fiber having a half millimeter diameter, the potting compound 38 associated with the present invention has enabled the probe 21 to be bent along a radius less than one-quarter inch without breaking. Thus the failure mode of the fibers 27, 30 has been increased by a factor of twelve by potting the fibers with the compound 38. In a particular embodiment, the potting compound 38 will fill the channel 25 around the fibers 27, 30.

In an embodiment including the working lumen 34, it is desirable that this lumen 34 not be filled with the potting compound 38. For example, in the embodiment of FIG. 3, the probe 21 includes the fiber channel 25 and the inner wall 33 which define the working lumen 34. In such an embodiment, only the channel 25 is potted with the compound 38. In an embodiment such as that illustrated in FIG. 2, there is no inner wall but the potting compound 38 defines the working lumen 34 which extends through the channel 25.

The advantages associated with the potting compound 38 can best be understood with reference to FIG. 4. This Figure shows a typical optical fiber, such as the fiber 30, which may be a fused image fiber having a diameter of one-half millimeter. In the absence of any potting compound, the fiber 30 would respond to bending stresses by initially experiencing a degradation in its optical performance characteristics. Ultimately this progressive degradation would give rise to a failure mode for the fiber where the fiber would crack and eventually break. This failure mode could occur at a radius R as large as three inches. Of course optical performance would have degraded at a radius even greater than R.

In accordance with the present invention, the potting compound 38 distributes the bending stresses along the fiber 30 so that its optical performance characteristics are maintained even when the fiber is bent to a radius less than R. The failure mode for the potted fiber 30 does not occur until the fiber is bent along a significantly smaller radius r such as 0.25 inches. In this particular case, the performance characteristics of the fiber are increased by 1200% with the addition of the potting compound 38.

The nature of the potting compound 38 can also be of interest to the present invention. For example, it is generally desirable that this compound have some flexible characteristics. Furthermore, it has been found for example that a compound having a low durometer in a Shore range of either A or D, will provide the best properties for stress relief. Durometers less than Shore 72D are preferred. It is also desirable that the potting compound 38 at least initially have fluid characteristics in order to facilitate manufacture of the endoscope 10. For these reasons, epoxies have been found particularly desirable for the potting compound 38.

A particular epoxy manufactured by Epoxy Technology Inc. and marketed under the Model No. 310 has been found to exhibit these characteristics and also provide additional advantages. This particular compound has a long potting life so that it remains fluid for a significant period of time prior to curing. It is desirable that this potting be at least three hours; the Epotech #310 epoxy has a potting life of eight hours. This particular compound also has a durometer of about 70A upon curing. This not only gives the cured epoxy some elastic characteristics but also facilitates polishing the distal end 14 of the probe 21.

FIGS. 5–8 are associated with steps in preferred methods for manufacturing the endoscope 10. For example, the probe 21 illustrated in FIG. 5 has the cross-sectional configuration illustrated in FIG. 3. This probe 21 includes the outer tube 23 but also the inner wall 33 which defines the working lumen 34. Since it is desirable to pot only the channel 25 and not the working lumen 34, an initial step in a preferred process includes inserting a plug 41 into the working lumen 34 at the end of the probe 21. The optical fibers 27, 30 are then disposed within the channel 25. A funnel 43 is provided to closely engage the outer surface of the tube 23 at the end including the plug 41. With the probe 21 oriented vertically, the funnel 43 can be filled with the pre-cured potting compound 38 which is allowed to fill the channel 25 around the fibers 27, 30 by gravity feed.

Another method for potting the endoscope 10 is to fill a syringe 45 with the potting compound 38 and to inject this compound into the channel 25 of the probe 21. In this case it is desirable if the injection be introduced vertically upwardly into the channel 25 as illustrated in FIG. 8. By injecting in this direction, the compound 38 is forced against the flow of gravity to fill the channel 25 without the possibility of downward flow which may result in air pockets. This injection step may be facilitated in a particular method by providing a vacuum 47 at the opposite end of the probe 21.

In a further method of the invention, the potting may take place after the probe 21 is fixed to the handle assembly 18. In this case, the channel 25 may be filled from the proximal end 16 of the scope 10 using either the funnel 43 or the syringe 45.

In a particular method wherein the compound 38 includes an epoxy, it is desirable to include a step for curing the epoxy. In its post-cured state, the epoxy will have a more rigid configuration thereby facilitating polishing of the distal end 14 of the scope 10 in a customary manner, for example using a polisher 47.

It will be apparent that the concept of this invention extends beyond the specific embodiments and method steps illustrated and discussed. Many different cross-sectional configurations of the probe 21 will benefit from the potting of the fibers 27, 30. Also, many different types of potting compounds 38 may be useful in a particular embodiment and for a specific purpose. The characteristics desirable for this compound will depend not only on the configuration of the probe 21 and channel 25, but also the characteristics associated with the various types of fibers which may be used in the endoscope 10. In the methods of manufacture, different orientations of the probe 21 may be desirable. Other apparatus, such as the syringe 45 and funnel 43, may also be employed as well as various combinations of pressure and vacuum to introduce the potting compound 38 into the channel 25.

Due to the wide range of modifications which may be made to the particular disclosed embodiments and methods, one is urged to determine the scope of the invention only with reference to the following claims.

I claim:

1. A surgical instrument having an elongate configuration and extending from a proximal end to a distal end, the instrument comprising:
   a housing disposed at the proximal end of the instrument;
   a tube extending from the housing to the distal end of the instrument and defining with the housing at least one channel;
   at least one optical fiber disposed in the channel, the fiber having performance characteristics which substantially degrade when the fiber is bent along a first radius;
   means disposed around the fiber in the channel for forming a solid structure to relieve bending stresses in the fiber so that the fiber can be bent along a second radius shorter than the first radius without substantially degrading the performance of the fiber; and
   the means for forming a solid structure comprising an epoxy which fills the channel around the fiber.

2. The surgical instrument recited in claim 1 wherein the epoxy has a durometer with a Shore hardness less than 72D.

3. The surgical instrument recited in claim 2 wherein the Shore hardness is in the A range.

4. The surgical instrument recited in claim 3 wherein the Shore hardness is about 70A.

5. An endoscope having an elongate configuration and extending from a proximal end to a distal end, the endoscope comprising:
   a housing disposed at the proximal end of the endoscope;
   a tube extending from the housing to the distal end of the endoscope, portions of the tube defining a channel and having properties for bending along a first radius;
   an elongate element disposed in the channel of the tube, the element having properties for breaking when bent along a radius greater than the first radius;
   means in the tube for forming a solid structure around the elongate element to reinforce the elongate element and prevent the elongate element from breaking when bent along the first radius;
   the means for forming a solid structure includes a potting material which engages the elongate element in the channel; and
   the potting material including a cured epoxy having a durometer with a Shore hardness less than 72D.

6. The endoscope recited in claim 5 wherein the Shore hardness is in the A range.

7. The endoscope recited in claim 6 wherein the Shore hardness is about 70A.

8. An endoscope having a distal end and a proximal end, including:
   a handle assembly disposed at the proximal end of the endoscope;
   an elongate probe fixed to the handle assembly and extending distally of the handle assembly to the distal end of the endoscope, the probe having characteristics for being bent;
   at least one fiber disposed in the channel and having an adverse response to bending stresses associated with a particular bending radius of the probe;
   means disposed in the channel for forming a solid structure around the fiber to distribute the bending stresses along the fiber and inhibit the adverse response of the fiber to the particular bending radius of the probe;
   wherein
   the solid structure forming means includes a potting compound having a durometer not greater than Shore 70D.

9. The endoscope recited in claim 8 wherein the solid forming means includes a potting compound having a durometer in the Shore A range.

10. The endoscope recited in claim 9 wherein the potting compound has a durometer of about Shore 70A.

11. A method of making an endoscope having a proximal end and a distal end, the method comprising the steps of:
    providing an elongate tube extending to the distal end of the endoscope and defining at least one channel, the tube being bendable along at least a portion of the channel;
    inserting into the channel at least one optical fiber; and
    surrounding the optical fiber;
    surrounding the optical fiber with a potting medium forming a solid to relieve stress at least along the bendable portion of the channel to facilitate bending the fiber along a smaller radius of curvature than would otherwise be possible without the stress relief;
    wherein
    the surrounding step includes the steps of pressurizing the channel with a liquid to fill the channel with a liquid around the fiber, and allowing the liquid to solidify.

12. The method recited in claim 11 wherein during the providing step the elongate tube is provided with the one channel in the form of a fiber channel and a second channel in the form of a working channel, and prior to the surrounding step, the method further comprises the step of plugging the working channel to prevent the liquid from entering the working channel.

13. The method recited in claim 11 wherein during the pressurizing step, the channel is pressurized with a pre-cured epoxy and the method further comprises the step of curing the epoxy in the channel.

14. The method recited in claim 13, wherein the step of curing the epoxy is carried out while the tube is in an unbent condition.

15. The method recited in claim 11 wherein the surrounding step includes the steps of:

gravity feeding an uncured epoxy into the channel around the optical fiber; and curing the epoxy in the channel.

16. The method recited in claim 15 further comprising the step of polishing the epoxy and the tube at the distal end of the endoscope.

17. The method recited in claim 11 wherein the surrounding step includes the step of potting the channel with a curable epoxy.

* * * * *